United States Patent [19]

Steinbach et al.

[11] Patent Number: 4,724,204

[45] Date of Patent: Feb. 9, 1988

[54] DIAGNOSTIC DEVICE FOR THE DETECTION OF INCREASED DEHYDROGENASE OR OXIDASE AND THE USE THEREOF

[75] Inventors: Roland W. Steinbach, Cologne; Asok K. Roy, Berlin; Peter Krauss, Pulheim, all of Fed. Rep. of Germany

[73] Assignee: Medi-Pharma Vertriebsgesellschaft mbH, Sachsenring, Fed. Rep. of Germany

[21] Appl. No.: 523,400

[22] Filed: Aug. 15, 1983

[30] Foreign Application Priority Data

Aug. 23, 1982 [DE] Fed. Rep. of Germany ....... 3231288

[51] Int. Cl.$^4$ .......................... C12Q 1/32; A61F 13/16
[52] U.S. Cl. ........................................ 435/26; 435/25; 435/27; 435/28; 604/361; 604/362; 604/904
[58] Field of Search ...................... 435/26, 805, 25, 27, 435/28; 604/361, 362, 904

[56] References Cited

U.S. PATENT DOCUMENTS 4,266,022  5/1981  Lamprecht .......................... 604/904

FOREIGN PATENT DOCUMENTS 2045427  10/1980  United Kingdom .................. 435/28

OTHER PUBLICATIONS

Tietz, et al., Fundamentals of Clinical Chemistry, 1976, W. B. Saunders Co., pp. 576–580, 652–654.

*Primary Examiner*—Robert J. Warden
*Assistant Examiner*—Stephen C. Wieder
*Attorney, Agent, or Firm*—Dressler, Goldsmith, Shore, Sutker & Milnamow, Ltd.

[57] ABSTRACT

A diagnostic device for the detection of an increased concentration of dehydrogenases and/or oxidases in the fluids of humans, animals or plants, which consists of a carrier which bonds a redox dyestuff, and a substance mixture, adjusted to a pH value in the acid range, of the substrate corresponding to the particular dehydrogenase, a hydrogen donor compound and at least one redox dyestuff is described. The device has the peculiarity that the carrier contains polar groups and the substance mixture for detecting exclusively pathologically increased concentrations of the particular dehydrogenase and/or oxidase is adjusted to a pH value of below 5.0. The device is suitable for diagnosing malignant growths in very different organs, for example in the female genital area.

8 Claims, No Drawings

DIAGNOSTIC DEVICE FOR THE DETECTION OF INCREASED DEHYDROGENASE OR OXIDASE AND THE USE THEREOF

The invention relates to a diagnostic device for the detection of an increased concentration of dehydrogenases and/or oxidases, and the use of the device.

For each cytosolic dehydrogenase which passes into extracellular fluids in cases of pathological change in humans, animals or plants it is possible to determine empirically the pathological threshold value in these fluids. When testing for a pathological change, the physico-chemical parameters of the diagnosis system should be set up such that the pathological threshold value of the dehydrogenase or oxidase activity coincides with the transition point of an indicator, for example a redox dyestuff, under the diagnosis conditions. In the case of pathological changes in the properties of cell membranes, it is to be expected that various pyridine-dependent dehydrogenases, such as lactate dehydrogenase (LDH), alcohol dehydrogenase (ADH), glyceraldehyde 3-phosphate dehydrogenase, isocitrate dehydrogenase, glutamate dehydrogenase, glucose dehydrogenase and glucose 6-phosphate dehydrogenase, and/or flavin-dependent dehydrogenases and/or flavin-dependent oxidases, such as succinate dehydrogenase, glycerol 3-phosphate dehydrogenase and glucose oxidase, pass into the serum and into other extracellular fluids, and that a threshold value pathological for the diagnosis is in each case found for each dehydrogenase or oxidase.

In this context, pathological change includes, for example, the formation of malignant growth. The physico-chemical parameters of the diagnosis system can be set up, for example, in the following manner in order to match the transition point of a redox dyestuff to the particular pathological threshold value:

(a) The substrate of the particular dehydrogenase is used, for example lactate for LDH.
(b) The amounts of substrate taken and of the pyridine nucleotide employed at the same time are adjusted.
(c) The pH value and hence the position of the equilibrium of the reaction is adjusted, if necessary by means of a buffer system.
(d) A redox dyestuff (for example a leuco dyestuff which changes from colourless to coloured) with a redox potential under the diagnosis conditions of greater than the redox potential of the pyridine nucleotide system is chosen.
(e) An electron donor with a redox potential between that of the pyridine nucleotide system and that of the chosen redox dyestuff is chosen.
(f) As long as the equilibrium of the dehydrogenase reaction has not yet been established, a longer reaction time gives a higher concentration of the reduced pyridine nucleotide. Accordingly, the transition threshold of the redox dyestuff and hence the detection sensitivity of the diagnosis system can be established via the duration of the reaction.
(g) Different carriers can be chosen for the diagnosis system.

German Patent Specification No. 2,443,741 discloses a process for joint determination of the isozymes 4 and 5 of LDH, in which a mixture of a lactate and nicotinamide adenine dinucleotide (NAD) is brought into contact with the body fluid to be investigated. If an increased amount of LDH is present, it catalyses the reaction of the lactate with the dinucleotide to give the corresponding pyruvate and reduced nicotinamide adenine dinucleotide (NADH) according to the following equation:

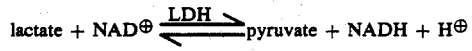

$$\text{lactate} + \text{NAD}^\oplus \xrightleftharpoons{\text{LDH}} \text{pyruvate} + \text{NADH} + \text{H}^\oplus$$

LDH occurs in human cells in the form of the isoenzymes 1, 2, 3, 4 and 5. In the case of certain specific pathological changes, increased LDH values occur, for example the isoenzymes 4 and 5 are increased in cases of malignant growth in the female genital area.

According to the printed publication, the reaction between the lactate and the NAD has to be carried out at a pH value of 6 to 6.5. For this purpose, the body fluid and/or the lactate and the test reagent containing NAD are adjusted to this pH range, if necessary using a buffer system. In cases where a body fluid, for example vaginal secretion, has a relatively low pH value, for example a pH value of 4, the test reagent can be adjusted to a pH value which exceeds the value 6.5, so that the desired pH value in the range from 6 to 6.5 results in the test reaction.

The reaction from left to right in the above equation is rendered visible by a secondary reaction. For this purpose, nitro blue tetrazolium chloride (NBT) and if appropriate phenazine methosulphate (N-methylphenazonium methyl-sulphate, 5-methylphenazonium methylsulphate, PMS), as a hydrogen donor or electron donor, are also added to the test reagent. The NADH formed according to the equation is oxidised by the NBT to NAD in the presence of the hydrogen donor or electron donor, the NBT being converted into the blue dyestuff nitro blue formazan [4,4'-(3,3'-dimethoxybiphenylenyl)-bis-2N-(2N'-p-nitrophenyl-C-phenyl-formazan)], and the enzymatic activity and presence of LDH or its isoenzymes thus being rendered visible.

The known process has been used to investigate vaginal secretion from women. The duration of the reaction between this secretion and the diagnosis reagent was preferably 15 to 30 minutes. Pathological changes in the female genital tract, for example carcinoma colli uteri, carcinoma corporis and carcinoma in situ, were detected.

False negative diagnoses of collum and cervix cancer of the order of size of on average 30% of the findings result in the screening of, for example, women for genital cancer by other known methods, for example cytology and colposcopy. These methods do not even include female genital cancers other than those mentioned above. There is therefore a great need to reduce this rate of error.

British Patent Specification No. 893,301 describes a colorimetric test for serum enzymes. A mixture containing a salt of lactic acid, diphosphopyridine nucleotide (nicotinamide adenine dinucleotide), diaphorase and 2,6-dichloroindophenol is described therein for the determination of lactate dehydrogenase in biological fluids. The pH value of the mixture should be in the range from 5 to 9.

However, according to this printed publication, a pH value of below 7.0 has evidently not seriously been taken into consideration, so that the range given as preferred is pH 7 to 8, and a specific embodiment example is carried out at a pH value of 7.4. Another point in the text states that the test is effected in a solution carefully buffered with a buffer of pH value 7. Finally, it has been found that this test cannot in fact be carried out at a pH value of 6. The use of tetrazolium salts in connection with the determination of LDH is not mentioned in the printed publication.

Moreover, this known test is envisaged quite generally for the determination of serum enzymes, but not for the detection of exclusively pathologically increased concentrations of dehydrogenases. Accordingly, the known test should already respond at very low enzyme concentrations, so that no differentiation between normal and pathologically increased dehydrogenase or oxidase values is possible.

The invention is based on the object of providing a diagnostic device for the detection of a pathologically increased concentration of dehydrogenases in fluids or secretions from humans, animals or plants. The device should ensure high diagnostic accuracy and be particularly suitable for diagnosing malignant growths. Moreover, the diagnosis should be capable of being carried out in as short a time as possible.

According to the invention, this object is achieved by a diagnostic device consisting of a carrier, which bonds a redox dyestuff, and a substance mixture, adjusted to a pH value in the acid range, of the substrate corresponding to the particular dehydrogenase, a hydrogen donor compound and at least one redox dyestuff. The device is characterised in that the carrier has polar groups and the substance mixture for detecting exclusively pathologically increased concentrations of the particular dehydrogenase is adjusted to a pH value of below 5.0.

The diagnostic device is particularly suitable for diagnosing pathological changes accompanied by an increase in the concentration of dehydrogenases in extracellular fluids. Such concentration changes occur even in the early stages of malignant growths, in which the prospect of successful therapy is still particularly great. The diagnostic device gives an indication of malignant growths on very different organs. Thus, inter alia, carcinomas on typical female organs, such as in the female genital area, can be detected. Infections by bacteria, parasites and fungi can also be detected by means of the device.

A particular advantage of the diagnostic device is its high prognosis value of the diagnoses. For example, in series experiments on women with histologically confirmed carcinomas in the genital area, it has been found that only less than 10% of all the diagnoses are falsely negative for stages I to IV.

There is also the advantage that when the diagnostic device is used intracorporally, for example as a tampon in the vagina, it is tolerated very well and leads to no irritation of the mucus membrane. This is particularly surprising, since, against all expectations, no transfer of the dyestuff formed into the mucus membrane can be detected.

In connection with this dyestuff formation, specific investigations, in which, for example, tissue sections have also been included, have shown that, surprisingly, the dyestuff remains on the carrier material during and after its formation and therefore induces no harmful secondary reactions in or on the body of the patient examined.

These advantages render the diagnostic device particularly useful for the desirable screening tests of health policy in which there must be not only maximum diagnostic reliability but also maximum safety from harmful secondary reactions of the diagnosis method, coupled with a method which is as simple as possible.

The outstanding properties of the diagnostic device are to be attributed to the particular combination of a carrier with polar groups and a low pH value of the substance mixture on the carrier. It is surprising that precisely this combination permits differential diagnosis recording pathological cases with high accuracy.

The great importance of the carrier for the functioning of the diagnostic device manifests itself, for example, in the fact that if no carrier is used, the colour reaction of the substance mixture with a liquid containing a pathologically increased dehydrogenase concentration does not proceed in the low pH range mentioned.

The fluid used for the diagnosis can originate from very different areas in humans, animals or plants. For example, vaginal secretion can be used to test for malignant neoplasms in the area of the genital organs of women. The diagnostic device can, however, also be used, for example, on blood serum, gastric and intestinal juice, bile, bronchial, prostatic and urethal secretion and sputum.

If the dehydrogenase to be detected is LDH, sodium lactate is preferably employed. However, other corresponding compounds, for example potassium lactate or calcium lactate, can also be used.

The hydrogen donor compound is a substance which assists the reduction of the redox dyestuff, for example a tetrazolium salt. Examples of such hydrogen donor compounds are NAD, nicotinamide adenine dinucleotide phosphate (NADP), flavin adenine dinucleotide (FAD) and flavin mononucleotide (FMN). However, other compounds with which the expert is familiar and which, for example, in place of NAD, can be converted into a reduced form corresponding to NADH in the conversion of lactate into pyruvate illustrated by the above equation, can also be used.

The substance mixture on the carrier contains at least one redox indicator, preferably a redox dyestuff, in order to render a dehydrogenase concentration above the pathological threshold value visible in a fluid to be examined.

Suitable dyestuff components include, for example, tetrazolium salts, benzidine dyestuffs, indophenols, such as 2,6-dichloroindophenol or dibromoindophenol, and ABTS. Particular appropriate tetrazolium salts are as follows: NBT, TNBT, MTT, INT, BT, TV, TT, NT, trinitro-TT, dinitro-TT, tetranitro-NT, tetranitro-BT, nitro-BT-methyl (methoxy group substituted by the methyl group), dinitro-TV, 3-(4-biphenylyl)-2,5-di-p-nitrophenyl-tetrazolium chloride, nitro-NT, tetranitro-BT$_{1/2}$ (symmetrically divided tetranitro-BT), nitro-BT, 3-(3,3'-dimethoxy-4-biphenylylene-2-p-nitrophenyl-5-phenyltetrazolium chloride, nitro-TV, nitro-TT, 3-p-iodophenyl-5-nitrophenyl-2-phenyl-tetrazolium chloride, 5,5'-dinitro-NT, 5,5'-dinitro-BT, 5-nitro-TV, 5-nitro-TT, and 2-(3-methoxy-4-phenyl)-5-p-nitrophenyl-3-phenyltetrazolium chloride.

In the above list:
NBT=3,3'-(3,3'-dimethoxy-4,4'-biphenylene)-bis-(2-p-nitrophenyl-5-phenyl-2H-tetrazolium chloride)
TNBT=3,3'-(3,3'-dimethoxy-4,4'-bisphenylene)-bis-(2,5-p-nitrophenyl-2H-tetrazolium chloride)
MTT=3-(4,5-dimethyl-2-thiazolyl)-2,5-diphenyl-2H-tetrazolium bromide
INT=2-p-iodophenyl-3-p-nitrophenyl-5-phenyl-2H-tetrazolium chloride BT=3,3'-(3,3'-dimethoxy-4,4'-biphenylene)-bis-(2,5-diphenyl-2H-tetrazolium chloride)

TV=3α-naphthyl-2,5-diphenyl-2H-tetrazolium chloride

TT=2,3,5-triphenyl-2H-tetrazolium chloride

NT=3,3'-(4,4'-biphenylene)-bis-(2,5-diphenyl-2H-tetrazolium chloride)

ABTS=2,2'-Azino-bis[3,3'-ethyl-benzthiazolin-6,6'-sulfonic-acid]

Using the above tetrazolium salts, the colour transition in the diagnostic device can be particularly easily adjusted to the pathological threshold value of the dehydrogenases to be detected. Tetrazolium salts, in particular NBT, are therefore preferred as the redox dyestuffs.

The substance mixture on the carrier of the diagnostic device has a pH value of below 5.0, preferably of 3.0 to below 5.0, in particular of 4.5. It is surprising that the reaction catalysed using the device, for example by the LDH, still proceeds in a low pH range of this nature, since, as can be seen from the above equation, hydrogen ions are liberated in the conversion of the lactate into the pyruvate. It would therefore have been expected that if the hydrogen ion concentration is further increased to beyond a pH value of 6.0, as is known from German Patent Specification No. 2,443,741, the reaction mentioned proceeds even more slowly or not at all, or the equilibrium shown in the equation is shifted towards the left. Contrary to these expectations, however, the reaction proceeds in the desired manner without visibly slowing down, the diagnostic accuracy of the device according to the invention, as mentioned, in addition also being improved in comparison with known methods.

The desired pH value of the substance mixture can be established in the customary manner, for example by adding hydrochloric acid and/or phosphoric acid.

According to a preferred embodiment of the diagnostic device, the substance mixture contains a buffer system for establishing and/or maintaining the pH value. When the diagnostic device is used, the reaction medium is thereby kept in a favourable pH range, even if the fluid investigated has a pH value which deviates from this range.

The buffer system is preferably in the form of triethanolamine hydrochloride or in the form of a non-equivalent mixture of triethanolamine and hydrogen chloride. The hydrogen chloride is employed, for example, in the form of hydrochloric acid.

However, other buffer systems, for example a phosphate buffer, can also be used as long as they do not lead to undesirable side reactions. Suitable buffer systems are known to the expert.

According to an advantageous development of the diagnostic device, the substance mixture additionally contains a compound which acts as a hydrogen donor or electron donor. This compound catalyses the reduction of, for example, a tetrazolium salt to the corresponding coloured formazan. For this, the hydrogen donor or electron donor must have a redox potential between the redox potential of the redox system employed according to the invention (for example the NAD/NADH system) and the redox potential of the redox dyestuff (for example the tetrazolium salt).

Particular examples of compounds having such an action are phenazine methosulphate (PMS), diaphorases, meldola's blue and menadione. Other appropriate compounds are known to the expert.

The equation which follows illustrates, by way of example, the reactions which proceed when the diagnostic device is used, if the redox system NAD/NADH, PMS, as the electron donor, and the tetrazolium salt NBT are employed:

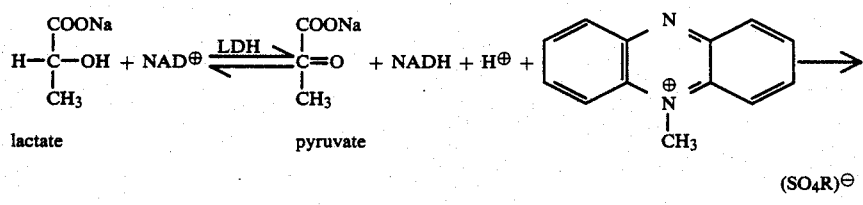

lactate    pyruvate phenazine methosulphate

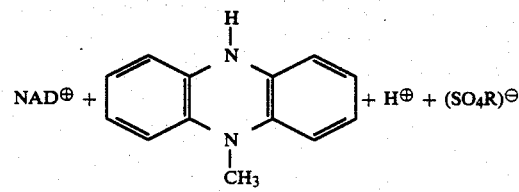

N—methyldihydrophenazine

-continued

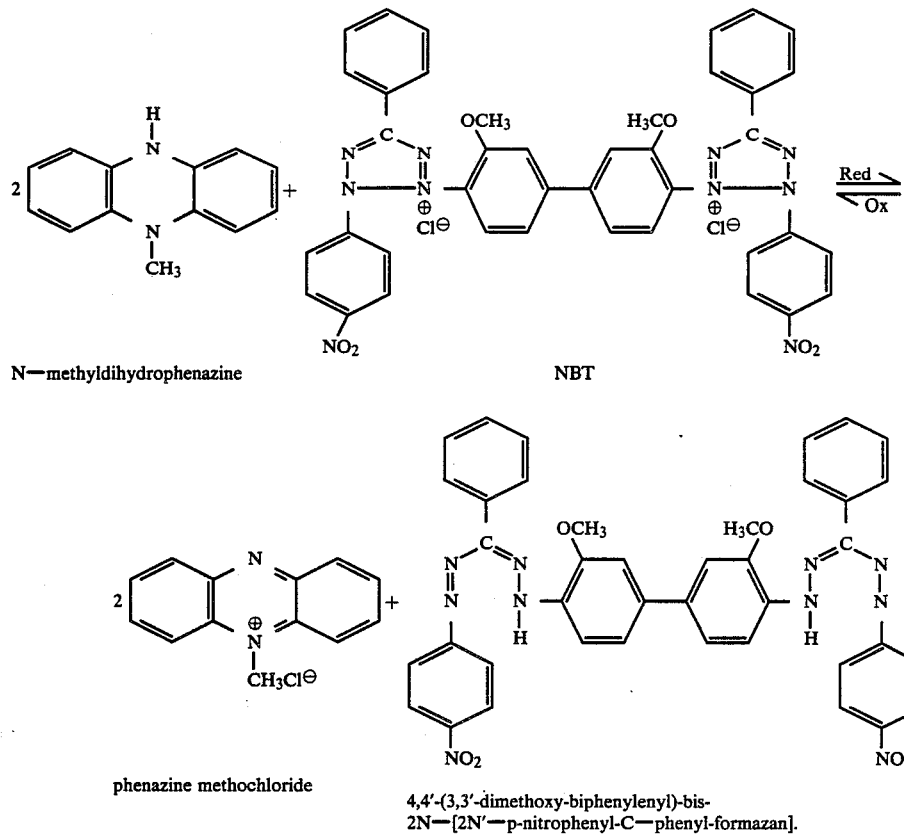

N—methyldihydrophenazine

NBT phenazine methochloride 4,4'-(3,3'-dimethoxy-biphenylenyl)-bis-
2N—[2N'—p-nitrophenyl-C—phenyl-formazan].

Carriers in the form of tampons of cellulose fibres have proved particularly suitable for diagnostic devices envisaged for detecting carcinomas in the female genital area. When used, the tampons are inserted into the vagina and thus enable a reaction between the substance mixture on the tampon and the vaginal secretion to take place. However, the test can also be carried out extracorporally, for example by bringing a sample of vaginal secretion into contact with the impregnated tampon outside the body.

In principle, however, other forms of carrier, such as small rods or films, can also be used.

The material of the carrier can be natural and/or synthetic, and can have, for example, a fibrous or granular structure or another type of structure. In all cases, the carrier has polar groups.

If the carrier of the diagnostic device is, for example, a tampon, the device is suitable not only for intracorporal diagnosis but also for extracorporal diagnosis. In the latter case, the fluid to be examined or the body secretion to be examined is simply brought into contact with that area of the tampon which contains the substance mixture mentioned.

The invention also relates to the use of the diagnostic device for early diagnosis of pathological changes, in particular malignant diseases, in humans, animals and plants.

The diagnostic device is preferably used for intracorporal or extracorporal detection of a pathologically increased concentration of dehydrogenases in extracellular human, animal or vegtable fluids, the substance mixture on the carrier being reacted with the fluid to be investigated, with the proviso that the reaction of the substance mixture with the fluid to be investigated is carried out for at most 10 minutes. Optimum results are obtained if this time is 5 to 7 minutes.

This applies in particular to the case where the carrier of the diagnostic device is a tampon which, for the diagnosis, is inserted into the vagina of a woman to be examined. The residence time of the tampon in the vagina then corresponds to the above-mentioned times. If the residence time is more than 10 minutes, a colour reaction may occur on the tampon in individual cases even if there is no pathological change in the woman examined. It is therefore essential that the residence time chosen is not too long.

The residence time of 5 to 7 minutes which is optimum in the context of the invention is considerably shorter than the preferred residence time of 15 to 30 minutes according to German Patent Specification No. 2,443,741. This is of particular importance for ease of carrying out the test in practice.

It has also proved particularly advantageous if the patient walks about during the residence time of the tampon in order to effect more intensive contact between the tampon and the mucus membrane of the vagina.

It has also been found that fluids which are to be examined for a pathologically increased dehydrogenase concentration can have very different pH values. For example, pH values of 3.9 to above 7 were measured in the vaginal secretion of women with pathological changes in the area of the genital organs. Surprisingly, the diagnostic device according to the invention can be easily adjusted to such reaction conditions without losing diagnostic accuracy. For example, if a fluid to be examined has a pH value of 5.0 or more, this value can be reduced for the reaction during the diagnosis in the desired manner by means of a buffer system, adjusted to a relatively low pH value, in the substance mixture contained in the diagnostic device.

The example which follows illustrates the invention.

EXAMPLE

In a series dilution in various hospitals, the accuracy of the diagnostic device with a tampon as the carrier was investigated on 486 women with diagnostically confirmed carcinomas in the area of the genital organs. In Table 1 which follows, the distribution of the diagnosis groups amongst the various age groups is given in absolute figures and percentages. The column "N.D." (=no data) relates to cases where the hospital carrying out the investigation provided no data for this age distribution.

stomach, sigmoid carcinoma, carcinoma of the rectum, carcinoma of the urinary bladder and pulmonary carcinoma. The neoplasms were predominantly included in the study because they had attacked the genitals invasively or by metastases.

Benign tumours: ovarian fibroma, ovarian and parovarian cysts, uterus myomatosus, corpus polypus, abdominal cysts and leiomyoblastoma.

Inflammations: salpingitis, tubo-ovarian abscess, cervicitis, colpitis, vaginitis, vulvitis and chronic pyelonephritis.

Residual diagnostic group: lower abdominal haematoma, and menopausal haemorrhaging, without indication of a diagnosis and with no pathological findings.

In the context of this investigation, the vaginal pH values of the patients were also measured. Results are summarised in the following Table II:

TABLE 1

| | Age distributions according to diagnosis groups. | | | | | | | | | | | | | |
|---|---|---|---|---|---|---|---|---|---|---|---|---|---|---|
| | Age Groups (years) | | | | | | | | | | | | | |
| | under 30 | | 30 to under 40 | | 40 to under 50 | | 50 to under 60 | | 60 to under 70 | | ≧70 | | N.D. | | Total | |
| Diagnosis groups | abs. | % | abs. | % | abs. | % | abs. | % | abs. | % | abs. | % | abs. | % | abs. | % |
| 1. Carcinoma of the breast | 1 | 2 | 5 | 8 | 14 | 21 | 12 | 18 | 13 | 20 | 14 | 21 | 7 | 11 | 66 | 100 |
| 2. Cancer of the ovary | 3 | 4 | 3 | 4 | 9 | 13 | 25 | 35 | 12 | 17 | 8 | 11 | 11 | 15 | 71 | 100 |
| 3. Corpus carcinoma | 0 | 0 | 1 | 2 | 2 | 3 | 16 | 22 | 29 | 40 | 14 | 19 | 10 | 14 | 72 | 100 |
| 4. Cervical cancer | 2 | 1 | 27 | 15 | 19 | 10 | 32 | 17 | 43 | 23 | 40 | 22 | 22 | 12 | 185 | 100 |
| 5. Vaginal carcinoma | 0 | 0 | 0 | 0 | 2 | 10 | 3 | 15 | 3 | 15 | 9 | 45 | 3 | 15 | 20 | 100 |
| 6. Cancer of the vulva | 0 | 0 | 0 | 0 | 0 | 0 | 1 | 8 | 3 | 25 | 5 | 42 | 3 | 25 | 12 | 100 |
| 7. Other malignant growths | 0 | 0 | 0 | 0 | 2 | 11 | 2 | 11 | 6 | 33 | 6 | 33 | 2 | 11 | 18 | 100 |
| 8. Benign tumours | 1 | 5 | 2 | 9 | 2 | 9 | 6 | 27 | 4 | 18 | 4 | 18 | 3 | 14 | 22 | 100 |
| 9. Inflammations | 2 | 17 | 4 | 33 | 1 | 8 | 4 | 33 | 1 | 8 | 0 | 0 | 0 | 0 | 12 | 100 |
| 10. Residual diagnostic group | 0 | 0 | 0 | 0 | 3 | 38 | 1 | 13 | 1 | 13 | 2 | 25 | 1 | 13 | 8 | 100 |
| Total | 9 | 1.9 | 42 | 8.6 | 54 | 11.1 | 102 | 21.0 | 115 | 23.7 | 102 | 21.0 | 62 | 12.8 | 486 | 100.0 |

N.D. = no data
abs. = absolute number
% = percentage, corresponding to the absolute number

TABLE II

| | pH values | | | | | | | | | | | | | |
|---|---|---|---|---|---|---|---|---|---|---|---|---|---|---|
| N.D. | | <3 | | 3 to <4 | | 4 to <5 | | 5 to <6 | | 6 to <7 | | ≧7 | | Total | |
| abs. | % | abs. | % | abs. | % | abs. | % | abs. | % | abs. | % | abs. | % | abs. | % |
| 59 | 12.1 | 2 | 0.4 | 1 | 0.2 | 67 | 13.8 | 124 | 25.5 | 63 | 13.0 | 170 | 35.0 | 486 | 100.0 |

Explanation of the individual diagnostic groups:

Cervical cancer: this comprises the diagnostic term for cancer of the collum, cervix and portio.

Carcinomas in other localisations and sarcomas: urethral carcinoma, sarcoma of the breast, malignant teratoma, uterine sarcoma, lymphosarcoma, fibrosarcoma, psammoma, malignant melanoma, carcinoma of the From the table, it can be seen that the investigation extended over a very wide pH range of the vaginal secretion.

The residence times of the tampon are given in minutes in the following Table III. These are in each case to be understood as the time a diagnosis tampon remains in the vagina.

TABLE III

| | Tampon Residence Times (Minutes) | | | | | | | | | | | |
|---|---|---|---|---|---|---|---|---|---|---|---|---|
| N.D. | | 4 | | 5 | | 6 | | 7 | | ≧8 | | Total | |
| abs. | % | abs. | % | abs. | % | abs. | % | abs. | % | abs. | % | abs. | % |
| 9 | | 8 | | 84 | | 129 | | 239 | | 17 | | 486 | |

TABLE III-continued

| | Tampon Residence Times (Minutes) | | | | | | | | | | | | |
|---|---|---|---|---|---|---|---|---|---|---|---|---|---|
| N.D. | | 4 | | 5 | | 6 | | 7 | | ≧8 | | Total | |
| abs. | % | abs. | % | abs. | % | abs. | % | abs. | % | abs. | % | abs. | % |
| | 1.9 | | 1.6 | | 17.3 | | 26.5 | | 49.2 | | 3.5 | | 100.0 |

The test results on the accuracy of the diagnostic agent for the various diseases are summarised in the following Tables IV, V, VI, VII, VIII, IX, and X.

Explanation:
0 = no data (−) = no colouration = diagnosis negative
(+) = pink = diagnosis still negative
+ = light blue with violet tinge = diagnosis positive
++ = blue = diagnosis positive
+++ = dark blue = diagnosis positive

TABLE IV

Test results of the patients with carcinoma of the breast according to tumour stages

| | Test results | | | | | | | | | | | | | |
|---|---|---|---|---|---|---|---|---|---|---|---|---|---|---|
| | 0 | | (−) | | (+) | | + | | ++ | | +++ | | Total | |
| Tumour stages | abs. | % | abs. | % | abs. | % | abs. | % | abs. | % | abs. | % | abs. | % |
| Stage I | 0 | 0 | 0 | 0 | 2 | 11 | 6 | 32 | 8 | 42 | 3 | 16 | 19 | 100 |
| Stage II | 0 | 0 | 0 | 0 | 0 | 0 | 3 | 33 | 4 | 44 | 2 | 22 | 9 | 100 |
| Stage III | 0 | 0 | 0 | 0 | 0 | 0 | 1 | 20 | 1 | 20 | 3 | 60 | 5 | 100 |
| Stage IV | 1 | 6 | 1 | 6 | 0 | 0 | 5 | 29 | 5 | 29 | 5 | 29 | 17 | 100 |
| Suspected carcinoma | 0 | 0 | 0 | 0 | 0 | 0 | 0 | 0 | 0 | 0 | 0 | 0 | 0 | 100 |
| No more detailed data | 1 | 6 | 0 | 0 | 0 | 0 | 9 | 56 | 4 | 25 | 2 | 13 | 16 | 100 |
| Total | 2 | 3.0 | 1 | 1.5 | 2 | 3.0 | 24 | 36.4 | 22 | 33.4 | 15 | 22.7 | 66 | 100.0 |

TABLE V

Test results of the patients with cancer of the ovary according to tumour stages

| | Test results | | | | | | | | | | | | | |
|---|---|---|---|---|---|---|---|---|---|---|---|---|---|---|
| | 0 | | (−) | | (+) | | + | | ++ | | +++ | | Total | |
| Tumour stages | abs. | % | abs. | % | abs. | % | abs. | % | abs. | % | abs. | % | abs. | % |
| Stage I | 0 | 0 | 0 | 0 | 0 | 0 | 0 | 0 | 2 | 67 | 1 | 33 | 3 | 100 |
| Stage II | 0 | 0 | 0 | 0 | 0 | 0 | 0 | 0 | 0 | 0 | 1 | 100 | 1 | 100 |
| Stage III | 0 | 0 | 0 | 0 | 0 | 0 | 0 | 0 | 3 | 43 | 4 | 57 | 7 | 100 |
| Stage IV | 0 | 0 | 2 | 5 | 3 | 7 | 4 | 10 | 14 | 34 | 18 | 44 | 41 | 100 |
| Suspected carcinoma | 0 | 0 | 0 | 0 | 0 | 0 | 0 | 0 | 1 | 100 | 0 | 0 | 1 | 100 |
| No more detailed data | 1 | 6 | 0 | 0 | 1 | 0 | 3 | 6 | 8 | 17 | 5 | 44 | 18 | 100 |
| Total | 1 | 1,4 | 2 | 2,8 | 4 | 5,6 | 7 | 9,9 | 28 | 39,4 | 29 | 40,9 | 71 | 100 |

TABLE VI

Test results of the patients with corpus carcinoma according to tumour stages

| | Test results | | | | | | | | | | | | | |
|---|---|---|---|---|---|---|---|---|---|---|---|---|---|---|
| | 0 | | (−) | | (+) | | + | | ++ | | +++ | | Total | |
| Tumour stage | abs. | % | abs. | % | abs. | % | abs. | % | abs. | % | abs. | % | abs. | % |
| Stage I | 3 | 13 | 2 | 8 | 0 | 0 | 2 | 8 | 9 | 38 | 8 | 33 | 24 | 100 |
| Stage II | 0 | 0 | 1 | 8 | 0 | 0 | 3 | 23 | 5 | 38 | 4 | 31 | 13 | 100 |
| Stage III | 0 | 0 | 0 | 0 | 0 | 0 | 1 | 20 | 1 | 20 | 3 | 60 | 5 | 100 |
| Stage IV | 0 | 0 | 0 | 0 | 0 | 0 | 1 | 17 | 3 | 50 | 2 | 33 | 6 | 100 |
| Dysplasia | 0 | 0 | 1 | 100 | 0 | 0 | 0 | 0 | 0 | 0 | 0 | 0 | 1 | 100 |
| Suspected carcinoma | 0 | 0 | 0 | 0 | 0 | 0 | 0 | 0 | 0 | 0 | 0 | 0 | 0 | 100 |

TABLE VI-continued

Test results of the patients with corpus carcinoma according to tumour stages

| Tumour stage | 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|---|
| No more detailed data | 0 | 0 | 0 | 0 | 2 | 9 | 5 | 22 | 13 | 57 | 3 | 13 | 23 | 100 |
| Total | 3 | 4.2 | 4 | 5.5 | 2 | 2.8 | 12 | 16.7 | 31 | 43.0 | 20 | 27.8 | 72 | 100.0 |

TABLE VII

Test results of the patients with cervical cancer according to tumour stages

| Tumour stage | | 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|---|---|
| Stage I | a | 1 | | 0 | | 2 | | 2 | | 6 | | 4 | | 15 | |
| | b | 0 | | 0 | | 0 | | 1 | | 0 | | 1 | | 2 | |
| | c | 0 | | 1 | | 1 | | 1 | | 3 | | 2 | | 8 | |
| | Sum | 1 | 4 | 1 | 4 | 3 | 12 | 4 | 16 | 9 | 36 | 7 | 28 | 25 | 100 |
| Stage II | a | 2 | | 1 | | 1 | | 0 | | 8 | | 10 | | 22 | |
| | b | 0 | | 0 | | 0 | | 0 | | 0 | | 1 | | 1 | |
| | c | 0 | | 0 | | 1 | | 0 | | 2 | | 11 | | 14 | |
| | Sum | 2 | 5 | 1 | 3 | 2 | 5 | 0 | 0 | 10 | 27 | 22 | 60 | 37 | 100 |
| Stage III | a | 0 | | 0 | | 0 | | 2 | | 13 | | 21 | | 36 | |
| | b | 0 | | 0 | | 0 | | 0 | | 0 | | 0 | | 0 | |
| | c | 0 | | 0 | | 0 | | 1 | | 2 | | 13 | | 16 | |
| | Sum | 0 | 0 | 0 | 0 | 0 | 0 | 3 | 6 | 15 | 29 | 34 | 65 | 52 | 100 |
| Stage IV | a | 0 | | 0 | | 0 | | 2 | | 3 | | 6 | | 11 | |
| | b | 0 | | 0 | | 0 | | 0 | | 0 | | 0 | | 0 | |
| | c | 0 | | 0 | | 0 | | 2 | | 0 | | 2 | | 4 | |
| | Sum | 0 | 0 | 0 | 0 | 0 | 0 | 4 | 27 | 3 | 20 | 8 | 53 | 15 | 100 |
| Dysplasia | a | 0 | | 0 | | 0 | | 0 | | 0 | | 0 | | 0 | |
| | b | 3 | | 2 | | 1 | | 2 | | 6 | | 2 | | 16 | |
| | c | 0 | | 0 | | 0 | | 0 | | 1 | | 1 | | 2 | |
| | Sum | 3 | 17 | 2 | 11 | 1 | 6 | 2 | 11 | 7 | 39 | 3 | 17 | 18 | 100 |
| Carcinoma in situ | a | 1 | | 0 | | 0 | | 0 | | 0 | | 0 | | 1 | |
| | b | 1 | | 0 | | 0 | | 1 | | 3 | | 4 | | 9 | |
| | c | 1 | | 1 | | 0 | | 0 | | 2 | | 1 | | 5 | |
| | Sum | 3 | 20 | 1 | 7 | 0 | 0 | 1 | 7 | 5 | 33 | 5 | 33 | 15 | 100 |
| Suspected carcinoma | a | 0 | | 0 | | 0 | | 0 | | 0 | | 0 | | 0 | |
| | b | 0 | | 0 | | 0 | | 0 | | 0 | | 0 | | 0 | |
| | c | 0 | | 0 | | 0 | | 0 | | 0 | | 0 | | 0 | |
| | Sum | 0 | 0 | 0 | 0 | 0 | 0 | 0 | 0 | 0 | 0 | 0 | 0 | 0 | 100 |
| No more detailed data | a | 0 | | 0 | | 0 | | 2 | | 6 | | 4 | | 12 | |
| | b | 0 | | 0 | | 0 | | 1 | | 1 | | 2 | | 4 | |
| | c | 1 | | 0 | | 0 | | 0 | | 2 | | 3 | | 6 | |
| | Sum | 1 | 4 | 0 | 0 | 0 | 0 | 3 | 14 | 9 | 41 | 9 | 41 | 22 | 100 |
| Total | a | 4 | | 1 | | 3 | | 8 | | 36 | | 45 | | 97 | |
| | b | 4 | | 2 | | 1 | | 5 | | 10 | | 10 | | 32 | |
| | c | 2 | | 2 | | 2 | | 1 | | 12 | | 34 | | 56 | |
| | Sum | 10 | 5,4 | 5 | 2,7 | 6 | 3,2 | 17 | 9,2 | 58 | 31,4 | 89 | 48,1 | 185 | 100,0 | a = cancer of the collum; b = cancer of the portio; c = cancer of the cervix

TABLE VIII

Test results of the patients with vaginal carcinoma according to tumour stages

| Tumour stage | 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|---|
| Stage I | 1 | 50 | 0 | 0 | 0 | 0 | 0 | 0 | 1 | 50 | 0 | 0 | 2 | 100 |
| Stage II | 0 | 0 | 0 | 0 | 0 | 0 | 0 | 0 | 0 | 0 | 1 | 100 | 1 | 100 |
| Stage III | 0 | | 0 | | 0 | | 0 | | 0 | | 0 | | 0 | |
| Stage IV | 0 | 0 | 0 | 0 | 0 | 0 | 0 | 0 | 1 | 50 | 1 | 50 | 2 | 100 |
| Dysplasia | 0 | | 0 | | 0 | | 0 | | 0 | | 0 | | 0 | |
| Carcinoma in situ | 0 | 0 | 0 | 0 | 0 | 0 | 0 | 0 | 0 | 0 | 1 | 100 | 1 | 100 |
| Suspected carcinoma | 0 | | 0 | | 0 | | 0 | | 0 | | 0 | | 0 | |

TABLE VIII-continued

Test results of the patients with vaginal carcinoma according to tumour stages

| Tumour stage | 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|---|
| No more detailed data | 0 | 0 | 0 | 0 | 0 | 0 | 2 | 14 | 6 | 43 | 6 | 43 | 14 | 100 |
| Total | 1 | 5 | 0 | 0 | 0 | 0 | 2 | 10 | 8 | 40 | 9 | 45 | 20 | 100 |

TABLE IX

Test results of patients with cancer of the vulva according to tumour stages

| Tumour stages | 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|---|
| Stage I | 0 | | 0 | | 0 | | 0 | | 0 | | 0 | | 0 | |
| Stage II | 0 | 0 | 0 | 0 | 1 | 33 | 1 | 33 | 1 | 33 | 0 | 0 | 3 | |
| Stage III | 0 | 0 | 0 | 0 | 0 | 0 | 0 | 0 | 0 | 0 | 2 | 100 | 2 | |
| Stage IV | 0 | 0 | 1 | 33 | 0 | 0 | 0 | 0 | 1 | 33 | 1 | 33 | 3 | |
| Dysplasia | 0 | | 0 | | 0 | | 0 | | 0 | | 0 | | 0 | |
| Carcinoma in situ | 0 | | 0 | | 0 | | 0 | | 0 | | 0 | | 0 | |
| Suspected carcinoma | 0 | | 0 | | 0 | | 0 | | 0 | | 0 | | 0 | |
| No more detailed data | 0 | 0 | 0 | 0 | 0 | 0 | 2 | 50 | 0 | 0 | 2 | 50 | 4 | |
| Total | 0 | 0 | 1 | 8 | 1 | 8 | 3 | 25 | 2 | 17 | 5 | 42 | 12 | 100 |

TABLE X

Test results of the patients belonging to the given diagnosis groups (with the exception of carcinomas in the area of the genital organs)

| Diagnosis group | 0 abs. | % | (−) abs. | % | (+) abs. | % | + abs. | % | ++ abs. | % | +++ abs. | % | Total | |
|---|---|---|---|---|---|---|---|---|---|---|---|---|---|---|
| Malignant growth (excluding those in the genital area) | 1 | 6 | 0 | 0 | 0 | 0 | 1 | 6 | 7 | 38 | 9 | 50 | 18 | 100 |
| Benign tumours | 2 | 9 | 3 | 13 | 5 | 23 | 2 | 9 | 5 | 23 | 5 | 23 | 22 | 100 |
| Inflammations (predominantly in the genital area) | 4 | 34 | 1 | 8 | 1 | 8 | 3 | 25 | 2 | 17 | 1 | 8 | 12 | 100 |
| Residual diagnostic group (partly no pathological findings) | 1 | 13 | 0 | 0 | 2 | 25 | 1 | 13 | 3 | 37 | 1 | 13 | 8 | 100 |

The test results found with carcinomas are summarised in the following Table XI.

TABLE XI

Test results on patients with carcinoma of the breast, ovarial carcinoma, cervical cancer and cancer of the vulva (only cases with the tumour stage characterization I, II, III and IV have been taken into consideration).

| 0 abs. | % | (−) abs. | % | (+) abs. | % | + abs. | % | ++ abs. | % | +++ abs. | % | Total abs. | % |
|---|---|---|---|---|---|---|---|---|---|---|---|---|---|
| 8 | | 9 | | 11 | | 38 | | 96 | | 130 | | 292 | |

TABLE XI-continued

Test results on patients with carcinoma of the breast, ovarial carcinoma, cervical cancer and cancer of the vulva (only cases with the tumour stage characterization I, II, III and IV have been taken into consideration).

| Test Results | | | | | | | | | | | | | |
|---|---|---|---|---|---|---|---|---|---|---|---|---|---|
| 0 | | (−) | | (+) | | + | | ++ | | +++ | | Total | |
| abs. | % | abs. | % | abs. | % | abs. | % | abs. | % | abs. | % | abs. | % |
| | 2.7 | | 3.1 | | 3.8 | | 13.0 | | 32.9 | | 44.5 | | 100.0 |

From this table, it can be seen that the diagnostic device has a hitherto unachievable high accuracy and is suitable for differential diagnosis. Statistical evaluation of the test results showed that, in all cases in which the presence of carcinomas (stage I to IV) in the genital area was confirmed by other examination methods (292 cases), the diagnostic device led to only 9.6% of false negative diagnoses.

We claim:

1. A diagnostic device for the detection of an increased concentration of lactate dehydrogenases in the fluids of humans, animals or plants which consists of: a carrier, and a substance mixture;
   said substance mixture comprising: a lactate substrate, a hydrogen donor compound, at least one redox dyestuff and buffered to a pH value of below 5.0; said carrier having polar groups and capable of binding said redox dyestuff.

2. Diagnostic device according to claim 1, wherein the pH value is adjusted to at least 3.0.

3. Diagnostic device according to claim 1, wherein the substance mixture contains a buffer system for establishing and maintaining the pH value.

4. Diagnostic device according to claim 3, wherein the buffer system is in the form of triethanolamine hydrochloride or in the form of a non-equivalent mixture of triethanolamine and hydrogen chloride.

5. Diagnostic device according to claim 1 to 4, wherein the substance mixture additionally contains a compound which acts as a hydrogen donor or electron donor.

6. Diagnostic device according to any one of claims 1 to 4, wherein the carrier consists of a tampon containing cellulose fibres.

7. Method for the detection of an increased concentration of lactate dehydrogenases in a body fluid which comprises contacting said body fluid with the diagnostic device of claim 1 for a period not exceeding 10 minutes and thereafter observing any color change in said device the color change being an indication of an increase in the concentration of lactate dehydrogenase.

8. Method in accordance with claim 7 wherein said contact time is from 5 to 7 minutes.

* * * * *

UNITED STATES PATENT AND TRADEMARK OFFICE
CERTIFICATE OF CORRECTION

PATENT NO. : 4,724,204            Page 1 of 2
DATED : February 9, 1988
INVENTOR(S) : Roland W. Steinbach, Asox Kumar Roy and Peter Krauss It is certified that error appears in the above-identified patent and that said Letters Patent is hereby corrected as shown below:

Bottom of columns 5 and 6, please replace the equations, as printed, with the following:

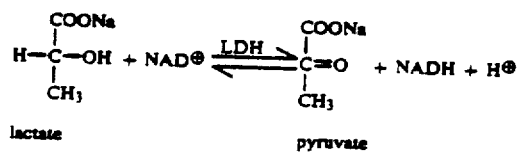

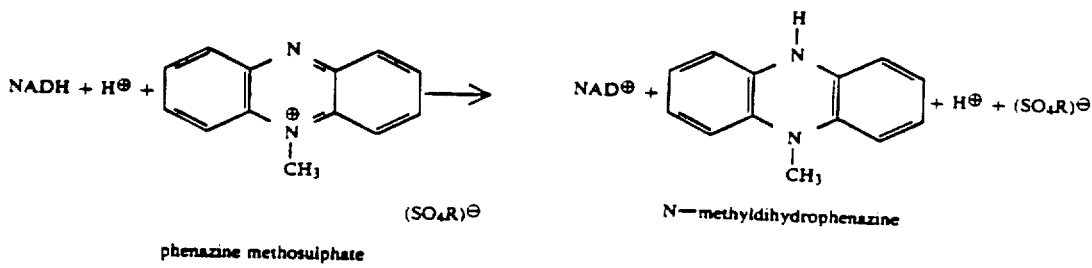

UNITED STATES PATENT AND TRADEMARK OFFICE
CERTIFICATE OF CORRECTION

PATENT NO. : 4,724,204

DATED : February 9, 1988

INVENTOR(S) : Roland W. Steinbach, Asox Kumar Roy and Peter Krauss

It is certified that error appears in the above-identified patent and that said Letters Patent is hereby corrected as shown below:

Columns 13 and 14, in TABLE VII, in the center vertical column, under "$\frac{+}{abs.\%}$" and in next to the last horizontal row, opposite "c", "1" should be --4--.

Signed and Sealed this

Eighteenth Day of April, 1989

Attest:

DONALD J. QUIGG

*Attesting Officer*

*Commissioner of Patents and Trademarks*